United States Patent [19]

Christensen et al.

[11] 4,078,067
[45] Mar. 7, 1978

[54] 3-(β-AMINOETHYLIDENE)-7-OXO-4-OXAAZABICYCLO[3.2.0]HEPTANE-2-CARBOXYLIC ACID AND DERIVATIVES THEREOF

[75] Inventors: Burton G. Christensen, Metuchen; Robert B. Morin, Warren; Edward Walton, Scotch Plains, all of N.J.

[73] Assignee: Merck & Co., Inc., Rahway, N.J.

[21] Appl. No.: 676,262

[22] Filed: Apr. 12, 1976

[51] Int. Cl.² .................. C07D 498/04; A61K 31/42
[52] U.S. Cl. ........................... 424/272; 260/250 AH; 260/295 F; 260/302 H; 260/306.8 A; 260/307 FA; 424/250; 424/263; 424/270
[58] Field of Search .................. 260/307 FA; 424/272

[56] References Cited
U.S. PATENT DOCUMENTS 3,950,352  4/1976  Wolfe ..................... 260/307 FA

OTHER PUBLICATIONS

Smith-"Open Chain Nitrogen Compounds"-vol. 2, W. A. Benjamin, Inc. (1966), pp. 250, 251, 254–255.

Primary Examiner—Raymond V. Rush
Attorney, Agent, or Firm—James A. Arno; Julian S. Levitt

[57] ABSTRACT 3-(β-aminoethylidene)-7-oxo-4-oxaazabicyclo [3.2.0]heptane-2-carboxylic acid and derivatives thereof having the structural formula:

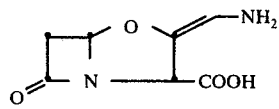

and the pharmaceutically acceptable salt, ester and amide derivatives thereof are disclosed to be useful as antibiotics. Also disclosed are processes for the preparation of such compounds; pharmaceutical compositions comprising such compounds; and methods of treatment comprising administering such compounds and compositions when an antibiotic effect is indicated.

5 Claims, No Drawings

3-(β-AMINOETHYLIDENE)-7-OXO-4-OXAAZABICYCLO[3.2.0]HEPTANE-2-CARBOXYLIC ACID AND DERIVATIVES THEREOF

BACKGROUND OF THE INVENTION

This invention relates to 3-(aminoethylidene)-7-oxo-4-oxaazabicyclo[3.2.0]heptane-2-carboxylic acid and its pharmaceutically acceptable salt, ester and amide derivatives which are useful as antibiotics. This invention also relates to processes for the preparation of such compounds; to pharmaceutical compositions comprising such compounds; and to methods of treatment comprising administering such compounds and compositions when an antibiotic effect is indicated.

The compounds of the present invention may be represented generically by the following structural formula (I):

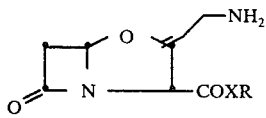
I wherein X is oxygen, sulphur or $NR^1$ ($R^1$ is hydrogen or R); R is hydrogen or, inter alia, is representatively selected from the group consisting of the pharmaceutically acceptable salt, ester, anhydride and amide moieties known in the bicyclic β-lactam antibiotic art—such moieties are enumerated representatively in greater detail below.

The compounds of the present invention, I, are related to the known antibiotic, 3-(β-hydroxyethylidene)-7-oxo-4-oxaazabicyclo[3.2.0]heptane-2-carboxylic acid which is also known as clavulanic acid (II):

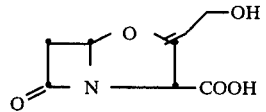
II

Clavulanic acid and its pharmaceutically acceptable salt and ester derivatives are fully disclosed, for example, in West German Patent Application (Offenlegungsschrift) No. 2,517,316 (1975). Clavulanic acid and its known salt and ester derivatives are useful starting materials for the preparation of the compounds of the present invention.

There is a continuing need for new antibiotics. For unfortunately, there is no static effectiveness of a given antibiotic because wide scale usage of any such antibiotic selectively gives rise to resistant strains of pathogens. In addition, the known antibiotics are effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide the novel class of antibiotics depicted by structure I, above. These antibiotics are active against a broad range of pathogens which representatively include both gram positive bacteria such as *S. aureus, S. pyogenes,* and *B. subtilis* and gram negative bacteria such as *E. coli., Proteus morganii,* and Klebsiella. Further objects of this invention are to provide chemical processes for the preparation of such antibiotics and their non-toxic pharmaceutically acceptable salt, ester and amide derivatives; pharmaceutical compositions comprising such antibiotics; and to provide methods of treatment comprising administering such antibiotics and compositions when an antibiotic effect is indicated.

DETAILED DESCRIPTION OF THE INVENTION

I. Identification of Radicals X and R:

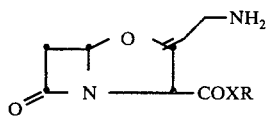
I

In the generic description of the invention (I, above), the radical COXR symbolizes in addition to the free carboxyl group (X is oxygen and R is hydrogen) the pharmaceutically acceptable salt, ester and amide derivatives of the free acid. Thus, X is selected from the group consisting of oxygen, sulfur, and $NR^1$ ($R^1$ is hydrogen or R); and R is selected from the group consisting of hydrogen, alkyl having 1–10 carbon atoms, straight or branched, such as methyl, ethyl, t-butyl, pentyl, decyl, and the like; carbonylmethyl, including phenacyl, p-bromophenacyl, p-t-butylphenacyl, acetoxyacetylmethyl, pivaloyloxyacetyl-methyl, carboxymethyl and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl alkoxyalkyl wherein the alkoxy moiety has 1–10 and preferably 1–6 carbon atoms, but can be branched, straight, or cyclic, and the alkyl moiety has 1–6 carbon atoms, such as methoxymethyl, ethoxymethyl, isopropoxymethyl, decyloxymethyl, ethoxypropyl, decyloxypentyl, cyclohexyloxymethyl and the like, alkanoyloxyalkyl wherein the alkanoyloxy moiety is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, and the like; acylthioalkyl, e.g., acetylthiomethyl, acetylthioethyl, pivaloylthiomethyl and the like; haloalkyl wherein halo is chloro, bromo, fluoro, or iodo, and the alkyl portion is straight or branched having 1–6 carbon atoms, e.g., 2,2,2-trichloroethyl, trifluoroethyl, 2-bromopropyl, diiodomethyl, 2-chloroethyl, 2-bromoethyl, and the like; alkenyl having 2–10 carbon atoms, either straight or branched, e.g., allyl, 3-butenyl, 4-butenyl, 4-pentenyl, 2-butenyl, 3-pentenyl, 3-methyl-2-butenyl, 2-methyl-2-propenyl, 1,4-cyclohexadien-1-methyl, and the like; alkynyl having 2–10 carbon atoms, either straight or branched, e.g., 3-pentynyl, propargyl, ethynyl, 3-butyn-1-yl, and the like; alkanoyl, either straight or branched, having 1–10 carbon atoms, such as pivaloyl, acetyl, propionyl, and the like; aralkyl or heteroaralkyl wherein alkyl has 1–3 carbon atoms, and hetero means 1–4 hetero atoms being selected from the group consisting of O, S, or N, such as benzyl, benzhydryl, and substituted benzyl, benzhydryl, or e.g., benzyl or benzhydryl substituted with 1–3 substitutents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p- benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butyoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as cyclic analogues thereof, 2,2-dimethyl-5-coumaranmethyl, 5-indanylmethyl, p-trimethylsilylbenzyl, 3,5-bis-t-butyoxy-4-hydroxybenzyl; 2-thienylmethyl, 2-furylmethyl, 3-t-butyl-5-isothiazolmethyl, 6-pivaloyloxy-3-pyridazinemethyl, 5-phenylthio-1-tetrazolylmethyl, or the like ) the use of the terms lower alkyl or lower alkoxy in this context means 1-4 carbon atom chain); or phthalidyl; or phenylethyl, 2-(p-methylphenyl)ethyl, and the arylthioalkyl analogues, aryloxyalkyl wherein aryl is preferably a phenyl ring having 0-3 substituents, preferably 0 or 1 substitutents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)phenoxymethyl, (4-benzyloxy)phenoxymethyl, (4-methyl)phenoxymethyl, (2-methoxy)phenoxymethyl, (1-phenoxy)ethyl, (4-amino)phenoxymethy, (4-methoxy)phenylthiomethyl, (4-chloro)phenylthiomethyl, phenylthioethyl; aryl wherein aryl is phenyl, 5-indanyl, or substituted phenyl having 0-3 substitutents, preferably 0 or 1 substitutent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and the alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl; alkylthioalkyl wherein the alkylthio portion has 1-10 and preferably 1-6 carbon atoms, but can be branched, straight, or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X is the

group. Representative of such amides, —CONR¹R are those wherein R¹ is selected from the group consisting of hydrogen, methyl, ethyl, phenyl, p-methoxyphenyl, benzyl, carboxymethyl, methylthioethyl and heteroaryl; also embraced by —COXR are anhydrides wherein R is acyl (the term "acyl" is defined for purposes of the present invention below) such as benzyloxycarbonyl, ethoxycarbonyl, benzoyl, and pivaloyl.

Particularly preferred esters are those wherein X is oxygen and R is aralkyl, aryloxyalkyl, aralkoxyalkyl, alkylthioalkyl, haloalkyl and alkenyl.

The most preferred COXR-bearing compounds of the present invention are those wherein (relative to structure I, above) X is oxygen, sulphur or NR¹ (R¹ is selected from the group consisting of hydrogen and lower alkyl); and R is selected from the group consisting of: alkyl, alkenyl, such as 2-methyl-2-propenyl, 3-methylbu-2-tenyl, 3-butenyl and the like; methylthio ethyl; benzyl and substituted benzyl, such as p-t-butylbenzyl, m-phenoxybenzyl, p-pivaloyloxybenzyl, p-nitrobenzyl and the like; pivaloyloxymethyl, 3-phthalidyl, acetoxymethyl, acylthioalkyl such as acetylthiomethyl, acetylthioethyl, pivaloylthiomethyl and the like.

Preparation of the compounds of the present invention is described below; however, it should be noted now that embodiments of the present invention wherein the radical —COXR is —COOH (the free acid) are conveniently prepared by operating (i.e., establishing the 3-($\beta$-amino ethylidene) side chain) on the clavulanic acid substrate in its protected form, i.e., wherein the carboxyl function of the clavulanic acid is blocked or protected by conventional carboxyl blocking groups known in the bicyclic $\beta$-lactam antibiotic art. Following the establishment of the 3-($\beta$-aminoethylidene) side chain, the free acid is prepared by deblocking of the carboxyl group by procedures known in the art such as hydrolysis or hydrogenation. Particularly suitable ester radicals for this purpose when X = O are substituted and unsubstituted benzyl such as p-nitrobenzyl.

Suitable blocking esters also include those selected from the following list which is representative and not intended to be an exhaustive list of possible ester groups, wherein X=O and R is given:

(i) $R=CR^aR^bR^c$ wherein at least one of $R^a$, $R^b$, and $R^c$ is an electron-donor e.g., p-methoxyphenyl, 2,4,6-trimethylphenyl, 9-anthryl, methoxy, $CH_2SCH_3$, tetrahydrofur-2-yl, tetrahydropyran-2-yl, or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R=CR^aR^bR^c$ wherein at least one or $R^a$, $R^b$, and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R = CR^aR^bR^c$ wherein at least two of $R^a$, $R^b$ and $R^c$ are hydrocarbon such as alkyl, e.g. methyl or ethyl, or aryl e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R = R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula $R^4_3SiX'$; $R^4_2SiX'_2$; $R^4_3Si.NR^4_2$; $R^4_3Si.NH.COR^4$; $R^4_3Si.NH.CO.NH.SiR^4_3$; $R^4NH.CO.NR^4.SiR^4_3$; or $R^4C(OSiR^4_3)$; $HN(SiR^4_3)_2$ wherein X' is a halogen such as chloro or bromo and the various groups $R^4$, which can be the same or different, represent hydrogen atoms or alkyl, e.g. methyl, ethyl, n-propyl iso-propyl; arly, e.g. phenyl; or aralkyl, e.g. benzyl groups.

In this connection, it is noted that preferred R "blocking groups" include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. More specifically, preferred R "blocking groups" including benzyl, phenacyl, p-nitrobenzyl, methoxymethyl, trichloroethyl, trimethylsilyl, tributyltin, p-methoxybenzyl, benzhydryl. These blocking groups are preferred since they are generally recognized as easily-removable blocking groups in the related antibiotic, bicyclic β-lactam art.

II. Preparation

The compounds of the present invention are conveniently prepared by reacting clavulanic acid or a protected derivative of clavulanic acid with an azide such as sodium azide, followed by reduction of the azide to the amino group. The following diagram illustrates this process:

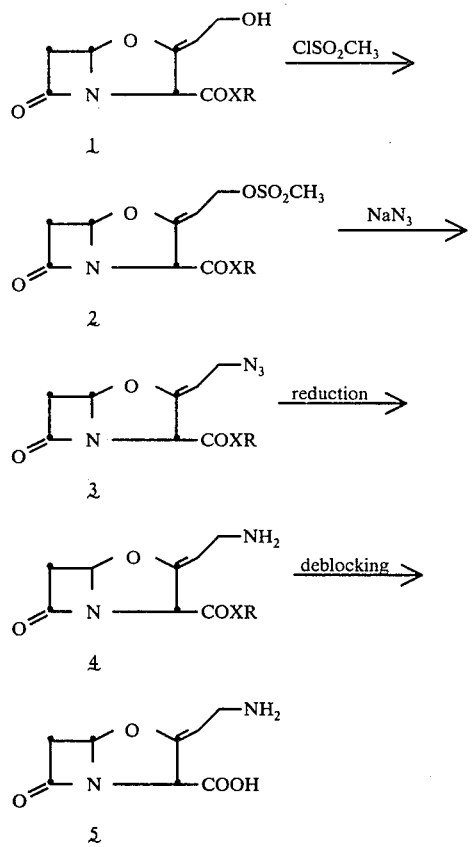

In words relative to the above reaction diagram, the preferred starting material is a suitably protected and activated clavulanic acid (2) such as an O-sulfonyl ester such as toluene sulfonyl or methane sulfonyl and suitable esters of the carboxyl function of clavulanic acid include in addition to easily removable blocking groups such as benzyl (when free acid embodiments of the present invention are ultimately desired) the above-enumerated list of pharmaceutically acceptable esters (—COXR, structure I, above). The preferred starting material (2) is conveniently prepared from (1) by treatment with a sulfonyl halide or anhydride such as methane sulfonyl chloride, toluene sulfonyl chloride, toluene sulfonic acid anhydride or the like in a solvent such as methylene chloride, tetrahydrofuran (THF), benzene or the like at a temperature of from about −80° to about 30° C. for from 1 to about 24 hours. The preferred starting material (2) is then treated with an azide such as sodium azide to form the azido species (3). Suitable solvents for the reaction (2→3) include any inert, polar organic solvent such as dimethylformamide (DMF), hexamethylphosphortriamide (HMPA), THF, glyme and the like. Typically the reaction is conducted at a temperature of from 5° to about 60° C for from about 1 to about 24 hours. The resulting azido species (3) is typically isolated by evaporation of solvent prior to the last step of the process comprising reduction of the azido function to the amino function. The reduction (3→4) may be conducted by any of a variety of well-known mild reduction means such as by hydrogenation or the use of other reducing agents such as hydrogen sulfide. A typical hydrogenation procedure for the reduction (3→4) involves treating 3 in a solvent such as ethanol, THF, dioxane, methanol, and the like under hydrogen (1 to 3 atmospheres) in the presence of a platinum metal catalyst such as platinum palladium or rhodium or their respective oxides for from 0.5 to 12 hours at a temperature of from 5° to 60° C. For such hydrogenation procedures, however, it is difficult to prevent the reaction (3→5) when the carboxyl moiety, XR, is selected from the list of easily removable blocking groups identified above. Thus, under circumstances when it is desired to effect only the reduction (3→3), the preferred means of selective reduction is by reducing agents, such as hydrogen sulfide wherein an aqueous or alcoholic solution of 3 is treated with hydrogen sulfide in the presence of triethylamine. The carboxyl deblocking step (4→5) may be effected by hydrogenation under conditions stated for the reduction of (3→4) or other deblocking procedures such as hydrolysis may be employed. Such carboxyl deblocking procedures are well-known in the analogous bicyclic β-lactam antibiotic art.

From the foregoing it is evident that the moiety —COXR (structure I, above) may be established on the starting material—its removal, being effected only when it is desired to obtain the free acid. Alternatively, the desired identity of —COXR may be established after the above-described establishment of the 3-(β-aminoethylidene) side chain according to the following reaction:

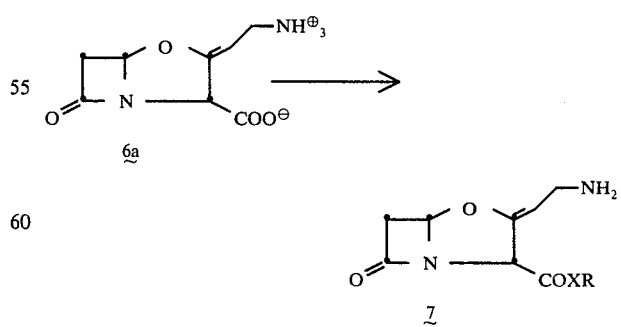

However, the preferred starting material for the derivatization of the carboxyl group is the azido species (6b) according to the following reaction scheme:

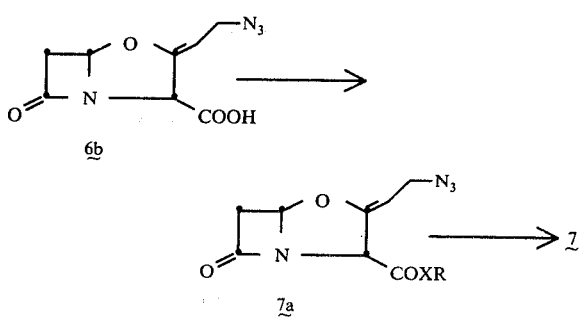

wherein the intermediate azido species 7a is reduced to the ultimate species 7 by treatment with hydrogen sulfide according to the procedure described above for the reduction of 3→4.

Relative to the transformation of the free acid to its esters and the like (6a or 6b→7) it is to be noted that the transformation is effected by conventional procedures known in the art. Such procedures include:

1. Reaction of the free acid (6b) with a diazoalkane such as diazomethane, phenyldiazomethane, diphenyldiazomethane and the like in an inert solvent such as dioxane, THF, halohydrocarbons, acetonitrile, ethylacetate, and the like at a temperature of from −78°, to 25° C., for from a few minutes to 2 hours.
2. Reaction of the metallic salts (e.g., Na, Li) of the acid (6b) with an activated alkyl halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, dimethylsulfoxide (DMSO), THF, dioxane, and the like at a temperature of from 20°, to 60° C., for from a few minutes to 4 hours.
3. Reaction of the free acid (6b) with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C to reflux for from 15 minutes to 18 hours, include $CHCl_3$, $CCl_4$, $CH_2Cl_2$ and the like.
4. Reaction of an acid anhydride of (6b) prepared by reacting the free acid (6b) with an acid chloride such as ethylchloroformate, benzylchloroformate and the like, with an alcohol such as those listed in (3) under the same conditions of reaction as given above for (3). The anhydride is prepared by reacting Ia and the acid chloride in a solvent such as tetrahydrofuran (THF), $CH_2Cl_2$ and the like at a temperature of from −20° C. to reflux for from 5 minutes to 2 hours.
5. Reaction of labile esters of (6b) such as the trimethylsilyl ester, dimethyl-t-butylsilyl ester or the like with RX′ wherein X′ is halogen such as bromo and chloro and R is as defined in a solvent such as THF, $CH_2Cl_2$ and the like at a temperature of from 0° C. to reflux for from 15 minutes to 16 hours in the presence of a base such as triethylamine, pyridine and the like.

Such trialkylsilyl esters of the carboxyl group, for example the trimethylsilyl ester, are conveniently prepared by treating (6b) with an excess of hexamethyldisilazane and a stoichiometric amount of trimethylchlorosilane at 25° C., with vigorous stirring under a $N_2$ atmosphere. The resulting $NH_4Cl$ is removed by centrifugation and the solvent is removed by evaporation to provide the desired silyl ester.

The amides of the present invention are most conveniently prepared by reacting the acid anhydride of (6b) with ammonia or with the amine of choice, e.g., the alkyl-, dialkyl-, aralkyl- or heterocyclic amines listed above.

The above-recited schemes of esterification are well-known in the related bicyclic β-lactam antibiotic art and indeed in all of general organic synthesis and it is to be noted that there is no undue criticality of reaction parameters in the preparation of the compounds of the present invention.

The compounds of the present invention are valuable antibiotics active against various gram-positive and gram-negative bacteria and, accordingly, find utility in human and veterinary medicine and in inanimate systems. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterial compounds of the invention may further be utilized as additives to animal feedstuffs for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding pharmaceutically acceptable salt, ester and amide derivatives may be employed in capsule form or as tablets, powders or liquid solutions or as suspensions or elixirs. They may be adminstered orally, intravenously or intramuscularly. Such pharmaceutically acceptable forms include salts of the free carboxyl group of the compounds of the present invention such as the alkali and alkaline earth metal ions such as sodium, and potassium and amines such as ammonium ion, xylocaine, procaine and dibenzylethylenediamine as well as the above-listed pharmaceutically acceptable esters and amides. However, with respect to the free acid embodiments of the present invention, it will be recognized that the compounds of the present invention exist as inner salts by virtue of the co-presence of the amino and carboxyl groups. Such pharmaceutically acceptable forms are prepared according to procedures well-known in the art.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases as ointments, creams, lotions, paints, or powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1 to about 99% of active material, the preferred range being from about 10-60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compounds in a slightly acidified sterile water solution or as the form of a soluble powder intended for solution.

The following examples further illustrate, but do not limit the product, process, compositional or method of treatment aspects of the present invention.

EXAMPLE 1

Preparation of Benzyl Clavulanate [3-(β-hydroxyethylidene)-7-oxo-4-oxaazobicyclo benzyl [3.2.0]heptane-2-carboxylate]

A mixture of 35 g crude sodium clavulanate and 50 ml of benzyl bromide in 150 ml of dimethylformamide is stirred at 25° C for 3.5 hrs. The reaction mixture is poured into 1 liter of ethylacetate and the mixture is filtered. The filtrate is concentrated in vacuo and the residual oil (35 g) is chromatographed on 750 g of silica gel using benzene-ethylacetate (2:1) as the eluting solvent. Fractions containing benzyl clavulanate are combined and concentrated in vacuo to give a residual oil (340 mg) of partially purified benzyl clavulanate. The crude product is rechormatographed on 30 g of silica gel in benzene-ethylacetate (3:1) and yields a total of 220 mg of benzyl clavulanate of improved purity. Final purification is accomplished by chromatography on 30 ml of LH-20 (Pharmacia Fine Chemicals, Inc.) in cyclohexane chloroform (1:1) which gives 160 mg of pure benzyl clavulanate. The product shows a single zone of $R_f$ 0.58 TLC in benzene-ethylacetate (1:1).

EXAMPLE 2

Preparation of O-Mesyl Benzyl Clavulanate [3-(β-Mesyloxyethylidene)-7-oxo-4-oxaazabicyclo[3.2.0]heptane-2-carboxylic acid benzyl ester]

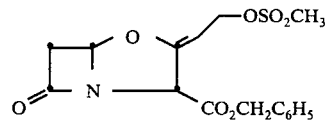

A solution of 289 mg (1 mmole) of benzyl clavulanate in 15 ml of methylene chloride is cooled to 0° C and treated with 320 mg (4 mmole) of pyridine and 192 mg (1.1 mmole) of methane sulfonic acid anhydride. After 20 hr the reaction solution is washed with three 3-ml portions of water. The methylene chloride solution is dried and concentrated in vacuo to give O-mesyl benzyl clavulanate.

EXAMPLE 3

Preparation 9-Deoxy-9-azido benzyl clavulanate [3-(β-azidoethylidene)-7-oxo-4-oxaazabicyclo-[3.2.0]heptane-2-carboxylic acid benzyl ester]

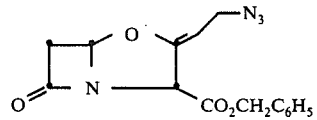

A solution of 367 mg (1 mmole) of O-mesyl benzyl clavulanate in 10 ml of dimethylformamide is treated with 72 mg (1.1 mmole) of $NaN_3$ and the mixture is stirred at 25° C. for 20 hr. The reaction solution is concentrated in vacuo and the residue is dissolved in 20 ml of methylene chloride and washed with three 5-ml portions of water. The methylene chloride solution is dried and concentrated in vacuo to give 9-deoxy-9-azido benzyl clavulanate.

EXAMPLE 4

Preparation of Benzyl 9-deoxy-9-amino clavulanate hydrochloride [benzyl (β-aminoethylidene)-7-oxo-4-oxaazabicyclo [3.2.0]heptane-2-carboxylate hydrochloride]

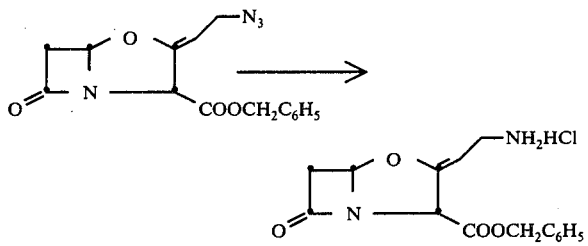

A stream of hydrogen sulfide is bubbled through a solution of 330 mg (1 mmole) of 9-deoxy-9-azido benzyl clavulanate and 200 mg of triethylamine, in 30 ml of ethanol, at 5° C for 3 min. A stream of nitrogen is then blown through the reaction solution to remove most of the hydrogen sulfide. The solution is treated with 1 ml of 1M hydrochloric acid and concentrated in vacuo to give a residue of benzyl 9-deoxy-9-amino clavulante hydrochloride.

EXAMPLE 5

Following the procedure of Examples 1 to 4 except that the benzyl bromide of Example 1 is replaced by an equivalent amount of an esterifying agent calculated to provide the ultimately desired ester, the compounds of Table 1 are obtained. Exceptions to established procedure are noted in the column labelled "Remarks".

TABLE 1

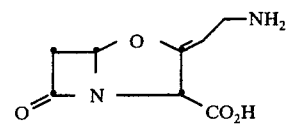

| Compound | X | R | Remarks |
|---|---|---|---|
| 1. | O | ![benzyl with t-butyl]  CH₃ / CH₃ / CH₃ | Starting material: p-t-butylbenzyl clavulanate, from p-t-butylbenzyl bromide |
| 2. | O | —CH₂OC(O)—C(CH₃)₃ | Starting material: pivaloyloxymethyl clavulanate, from pivaloyloxymethyl chloride |
| 3. | O | ![m-methoxybenzyl] OCH₃ | Starting material: m-methoxyethyl clavulanate, from m-methoxybenzyl bromide |
| 4. | O | —CH₂C(CH₃)=CH₂ | Starting material: methallyl clavulanate, from methallyl bromide |
| 5. | O | —CH₂CH=C(CH₃)₂ | Starting material: 3-methyl-2-butenyl clavulanate, from 3-methyl-2-butenyl bromide |

EXAMPLE 6

Preparation of 9-Deoxy-9-amino clavulanic acid [(β-aminoethylidene)-7-oxo-4-oxaazabicyclo [3.2.0]heptane-2-carboxylic acid]

A solution of 330 mg (1 mmole) of 9-deoxy-9-azido benzyl clavulanate in 40 ml of ethanol containing 150 mg of 10% palladium on carbon catalyst is stirred in an atmosphere of hydrogen (1 atmosphere of hydrogen) at a temperature of 25° C for 1 hour. The reaction mixture is filtered and the catalyst is washed with ethanol. The filtrate and washings are concentrated in vacuo to give a residue containing 9-deoxy-9-amino clavulanic acid.

EXAMPLE 7

Preparation of Sodium 9-Deoxy-9-azido clavulanate [Sodium(β-azidoethylidene)-7-oxo-4-oxaazabicyclo[3.2.0]heptane-2-carboxylate]

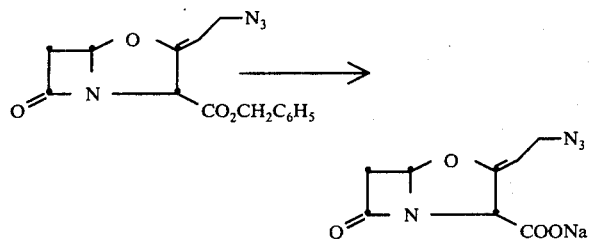

A solution 330 mg (1 mmole) of 9-deoxy-9-azido benzyl clavulanate in 10 ml of ethanol and 10 ml of water is treated with 84 mg (1 mmole) of NaHCO₃ and kept at 25° C. for 8 hrs. The reaction solution is concentrated to remove the ethanol and the aqueous residue is freeze-dried to give a residue of sodium 9-deoxy-9-azido clavulanate.

EXAMPLE 8

Preparation of Pharmaceutical Compositions

One such dosage form consists in mixing 120 mg. of 3-(β-aminoethylidene)-7-oxo-4-oxaazabicyclo[3.2.0]-heptane-2-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 3-(β-aminoethylidene)-7-oxo-4-oxaazabicyclo [3·2·0]-heptane-2-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 3-(β-aminoethylidene)-7-oxo-4-oxaazabicyclo [3-2-0]-heptane-2-carboxylic acid | 500 mg. |
| Diluent: Serile Water for Injection | 2 cc. |
| OPTHALMIC SOLUTION | |
| 3-(β-aminoethylidene)-7-oxo-4-oxaazabicyclo [3-2-0]-heptane-2-carboxylic acid | 100 mg. |
| Hydroxypropylmethyl Cellulose | 5 mg. |
| Sterile Water | to 1 ml. |
| OTIC SOLUTION | |
| 3-(β-aminoethylidene)-7-oxo-4-oxaazabicyclo [3-2-0]-heptane-2-carboxylic acid | 100 mg. |
| Benzalkonium Chloride | 0.1 mg. |
| Sterile Water | to 1 ml. |
| TOPICAL OINTMENT | |
| 3-(β-aminoethylidene)-7-oxo-4-oxaazabicyclo [3-2-0]-heptane-2-carboxylic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

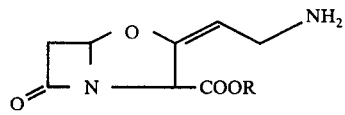

and the pharmaceutically acceptable salts thereof

2. A compound having the structure:

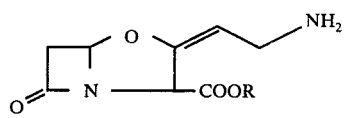

wherein R is selected from the group consisting of alkyl having 1 to 6 carbon atoms; pivaloyloxymethyl, halo- and perhaloalkyl having 1 to 6 carbon atoms wherein the halogen is chloro, fluoro or bromo; alkenyl having from 2 to 6 carbon atoms; benzyl, benzhydryl, p-t-butylbenzyl, p-bromobenzyl, phthalidyl, 5-indanylmethyl, phenyl, 5-indanyl, acetylthiomethyl, acetylthioethyl, pivaloythiomethyl, alkylthioalkyl, having 2 to 6 carbon atoms.

3. A compound according to claim 2 wherein R is selected from the group consisting of, methyl, t-butyl, pivaloyloxymethyl, 2,2,2-trichloroethyl, allyl, 3-methyl-2-butenyl, 2-methyl-2-propenyl, benzyl, benzylhydryl, p-t-butylbenzyl, phthalidyl, phenyl, 5-indanyl, acetylthiomethyl, acetylthioethyl, pivaloylthiomethyl, methylthiomethyl.

4. An antibiotic pharmaceutical composition comprising in unitary dosage form, a therapeutically effective amount of a compound according to claim 1 and a pharmaceutical carrier therefor.

5. An antibiotic pharmaceutical composition comprising in unitary dosage form, a therapeutically effective amount of a compound according to claim 2 and a pharmaceutical carrier therefor.

* * * * *